United States Patent [19]

Bentley et al.

[11] 4,349,551
[45] Sep. 14, 1982

[54] PENICILLIN DERIVATIVES AND COMPOSITIONS CONTAINING THEM

[75] Inventors: Peter H. Bentley; Kenneth D. Hardy; Peter H. Milner, all of Horsham, England

[73] Assignee: Beecham Group Limited, England

[21] Appl. No.: 271,007

[22] Filed: Jun. 5, 1981

[30] Foreign Application Priority Data

Jun. 6, 1980 [GB] United Kingdom ................. 8018577

[51] Int. Cl.³ .................. A61K 31/495; C07D 499/70
[52] U.S. Cl. .................................. 424/250; 260/239.1
[58] Field of Search ....................... 260/239.1; 424/250

[56] References Cited

U.S. PATENT DOCUMENTS 3,862,182  1/1975  Johnston ...................... 260/239.1 X
4,087,424  5/1978  Saikawa et al. ............... 260/239.1 X
4,215,118  7/1980  Preiss et al. .................... 260/239.1
4,235,774  11/1980 Preiss et al. .................... 260/239.1

Primary Examiner—Natalie Trousof
Assistant Examiner—Vera C. Clarke
Attorney, Agent, or Firm—Jacobs & Jacobs

[57] ABSTRACT

A compound of formula (I) or a pharmaceutically acceptable salt or in vivo hydrolyzable ester thereof:

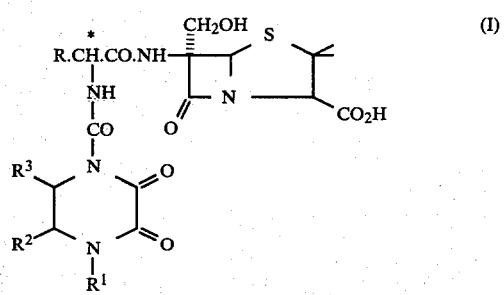

wherein
R is phenyl 4-hydroxy phenyl, or a 5- 6- membered heterocyclic ring containing up to three heteroatoms selected from oxygen, sulphur or nitrogen, optionally substituted with hydroxy, amino, halogen or $C_{1-6}$ alkoxy;
$R^1$ represents hydrogen or $C_{1-6}$ alkyl;
$R^2$ and $R^3$ are the same or different and represent hydrogen, $C_{1-6}$ alkyl, halogen, amino, hydroxy, or $C_{1-6}$ alkoxy.

Their preparation and use is described.

11 Claims, No Drawings

PENICILLIN DERIVATIVES AND COMPOSITIONS CONTAINING THEM

This invention relates to a class of penicillin derivatives which have antibacterial activity and are of value in the treatment of infections in animals, including man and poultry, caused by a wide range of organisms, particularly Gram-negative organisms. In particular the invention relates to a class of 6α-hydroxymethyl penicillin derivatives. The invention also relates to a process for the preparation of such compounds, and to pharmaceutical compositions comprising them.

British Patent Specification No. 1,339,007 discloses inter alia a class of 6-substituted acylamino penicillins of general formula (A):

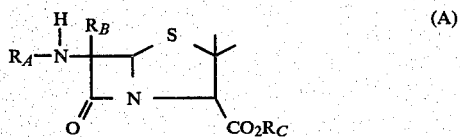

where $R_A$ represents an acyl group, $R_B$ is hydroxy or mercapto radical, a substituted or unsubstituted methoxy, ethoxy, methyl, ethyl, methylthio, or ethylthio radical, a carbamoyloxy, carbamoylthio, $C_{1-6}$ alkanoyloxy, $C_{1-6}$ alkanoylthio, cyano or carboxy radical or a derivative of a carboxy radical such as carbamoyl and $R_C$ is a hydrogen atom or a pharmaceutically acceptable esterifying radical or cation.

We have now found a class of 6-substituted acylamino penicillins which have a high level of antibacterial activity against gram-negative organisms.

According to the present invention there is provided a compound of formula (I) or a pharmaceutically acceptable salt or in vivo hydrolysable ester thereof:

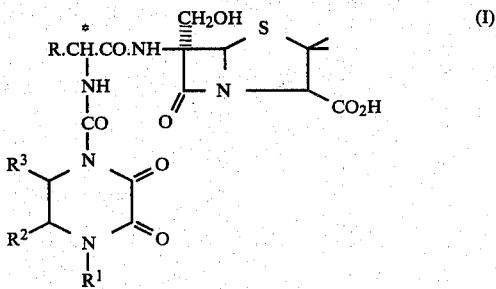

wherein
R is phenyl, 4-hydroxy phenyl, or a 5- or 6-membered heterocyclic ring containing up to three heteroatoms selected from oxygen, sulphur or nitrogen, optionally substituted with hydroxy, amino, halogen or $C_{1-6}$ alkoxy;
$R^1$ represents hydrogen or $C_{1-6}$ alkyl;
$R^2$ and $R^3$ are the same or different and represent hydrogen, $C_{1-6}$ alkyl, halogen, amino, hydroxy, or $C_{1-6}$ alkoxy.

The compounds of the present invention include the pharmaceutically acceptable esters of compound (I) which hydrolyse readily in the human body to produce the parent acid, for example acyloxyalkyl groups such as acetoxymethyl, pivaloyloxymethyl, α-acetoxyethyl, α-acetoxyethyl and α-pivaloyloxyethyl groups; alkoxycarbonyloxyalkyl groups, such as ethoxycarbonyloxymethyl and α-ethoxycarbonyloxyethyl; dialkylaminoalkyl groups such as dimethylaminomethyl, dimethylaminoethyl, diethylaminomethyl or diethylaminoethyl; and lactone groups such as phthalidyl or dimethoxyphthalidyl.

The compounds of the present invention also include the pharmaceutically acceptable esters of compound (I) which hydrolyse readily in the human body to produce the hydroxyl group of the 6-substituent, for example the formyl ester.

Suitable salts of the compound of formula (I) include metal salts e.g. aluminium, alkali metal salts such as sodium or potassium alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabietylamine ethylenediamine, or bases of the pyridine type such as pyridine, collidine or quinoline, or other amines which have been used to form salts with known penicillins.

The carbon atom marked * in formula (I) is asymmetric so that the compounds may exist as two optically active diastereoisomers. In general that prepared from the D-side chain exhibits the highest antibacterial activity.

In formula (I), the group R is preferably phenyl or 4-hydroxyphenyl, 2-thienyl, 3-thienyl or 2-amino-4-thiazolyl.

Suitable $C_{1-6}$ alkyl groups for the groups $R^1$, $R^2$ and $R^3$ include methyl, ethyl, n- and iso- propyl, n, sec-, iso- and tert-butyl. Preferably $R^1$ is ethyl. Preferably $R^2$ and $R^3$ are hydrogen.

Specific compounds within this invention include the following:

6,α-hydroxymethyl-6,β-[D,α'-(4-ethyl-2,3-dioxopiperazine-1-carbonylamino)-phenylacetamido]penicillanic acid;

6,α-hydroxymethyl-6,β-[D,α'-(4-ethyl-2,3-dioxopiperazine-1-carbonylamino)-p-hydroxyphenylacetamido]-penicillanic acid.

6,α-hydroxymethyl-6,β-[DL,-α'-(4-ethyl-2,3-dioxopiperazine-1-carbonylamino)-2-aminothiazole-4-acetamido]penicillanic acid.

The compounds of formula (I) may be prepared by reacting a compound of formula (II);

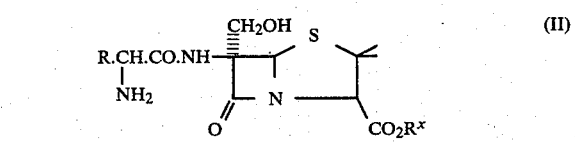

wherein the amino group is optionally substituted with a group which permits acylation to take place, R is as defined with respect to formula (I) and any reactive substituents may be protected, and $R^x$ is hydrogen or a carboxyl-blocking group, with an N-acylating derivative of an acid of formula (III).

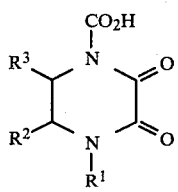
(III)

wherein $R^1$, $R^2$ and $R^3$ are as defined with respect to formula (I) above and any reactive groups may be protected; and thereafter, if necessary, carrying out one or more of the following steps:

(i) removing any carboxyl-blocking group $R^x$
(ii) removing any protecting groups on the side chain group;
(iii) converting the product into a salt or in vivo hydrolysable ester thereof.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula $-P.R^aR^b$ wherein $R^a$ is an alkyl, haloalkyl, aryl, aralkyl, alkoxy, haloalkoxy, aryloxy, aralkyloxy or dialkylamino group, $R^b$ is the same as $R^a$ or is halogen or $R^a$ and $R^b$ together form a ring; suitable such phosphorus groups being $-P(OC_2H_5)_2$, $-P(C_2H_5)_2$,

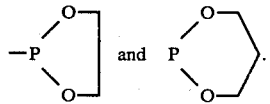

Suitable carboxyl-blocking derivatives for the group $-CO_2R^x$ in formula (II) include salts and ester derivatives of the carboxylic acid. The derivative is preferably one which may readily be cleaved at a later stage of the reaction. Suitable salts include metal salts, such as those with sodium, potassium and lithium, and tertiary amine salts, such as those with trilower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for $R^x$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, such as described above, an oxime radical of formula $-N=CHR°$ where $R°$ is aryl or heterocyclic, or an in vivo hydrolysable ester radical such as defined above.

The carboxyl group may be regenerated from any of the above esters by usual methods appropriate to the particular $R^x$ group, for example, acid- and base-catalysed hydrolysis, or by enzymically-catalysed hydrolysis, or by hydrogenation.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be affected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a $(C_{1-6})$-1,2,alkylene oxide-such as ethylene oxide or propylene oxide. The acylation reaction using an acid halide may be carried out at a temperature in the range $-50°$ C. to $+50°$ C., preferably $-20°$ to $+20°$ C., in aqueous or non-aqueous media such as aqueous acetone, aqueous tetrahydroform, ethyl, acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting a compound of formula IV:

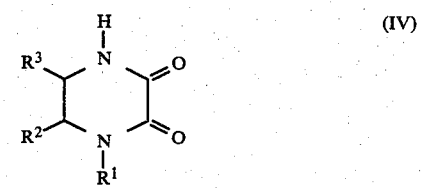
(IV)

wherein $R^1$, $R^2$ and $R^3$ are as defined with respect to formula (I) with a silylating agent and thereafter treating the N-silyl derivative with phosgene or carbonyl dibromide.

Suitable silylating agents include halosilanes or silazanes of the formulae.

$L_3$ Si U; $L_2$ Si $U_2$; $L_3$ Si $NL_2$; $L_3$Si NH Si $L_3$; $L_3$ Si.NH.COL; $L_3$ Si.NH.CO.NH.Si $L_3$; L NH.CO.NH.Si $L_3$;

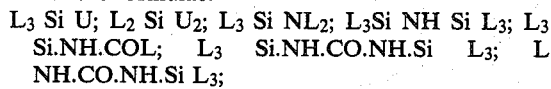
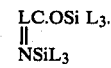

wherein U is a halogen and the various groups L which may be the same or different, each represents hydrogen or alkyl, alkoxy, aryl, or aralkyl. Preferred silylating agents are silyl chlorides, particularly trimethylchlorosilane, and dimethyldichlorosilane.

The intermediate compound of formula (II) may be prepared by reacting a compound of formula (V):

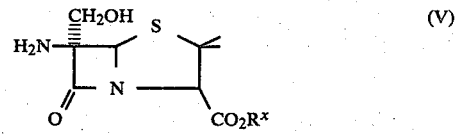
(V)

wherein the amino group is optionally substituted with a group which permits acylation to take place and $R^x$ is as defined with respect to formula (II) above, with an N-acylating derivative of an acid of formula (VI)

wherein R is as defined with respect to formula (I) and any reactive groups therein may be protected and $R^y$ is an amino-protecting group; and thereafter removing protecting group $R^y$.

Suitable N-acylating derivatives, carboxyl protecting groups and reaction conditions include those described hereinbefore.

Suitable amino-protecting groups $R^y$ are those well-known in the art which may be removed under conventional conditions without disruption of the remainder of the molecule.

The starting material of formula (V) is disclosed in British Pat. No. 1,366,682.

The compounds of formula (I) may also be prepared by reacting a compound of formula (V) as described hereinbefore with an N-acylating derivative of an acid of formula (VII):

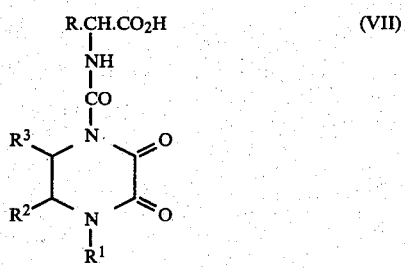

where R, $R^1$, $R^2$ and $R^3$ are as defined with respect to formula (I) and any reactive groups therein may be protected; and thereafter, if necessary, carrying out one or more of the following steps:

(i) removing any carboxyl-blocking group $R^x$
(ii) removing any protecting groups on the side chain group;
(iii) converting the product into a salt or in vivo hydrolysable ester thereof.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route, such as oral topical or parenteral. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration.

The compound of formula (I) may be the sole therapeutic agent in the compositions of the invention or a combination with other antibiotics or with a β-lactamase inhibitor may be employed. Advantageously the compositions also comprise a compound of formula (VIII) or a pharmaceutically acceptable salt or ester thereof:

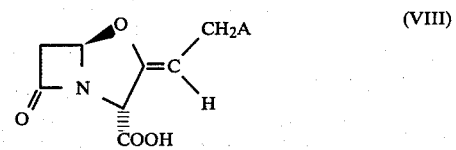

wherein A is hydroxyl, substituted hydroxyl, thiol, substituted thiol, amino, mono- or di-hydrocarbyl-substituted amino, or mono- or di-acylamino.

The following Examples illustrate the preparation of some of the compounds of this invention.

EXAMPLE 1

6,α-Hydroxymethyl-6,β-[D,α'-(4-ethyl-2,3-dioxopiperazine-1-carbonylamino)-phenylacetamido]penicillanic acid (a) Benzyl N-p-nitrobenzylidene-6-aminopenicillanate A solution of 6-aminopenicillanic acid benzyl ester (12.32 g, 40.3 mmol) and p-nitrobenzaldehyde (6.08 g, 40.3 mmol) in anhydrous toluene (200 ml) was stirred for 16 hours at room temperature over 4A molecular sieves. The reaction mixture was then filtered and the filtrate evaporated to dryness to leave a yellow oil. Trituration over ethanol afforded the crude product 12.8 g (72%) which was recrystallised from ethyl acetate/petroleum ether 60°–80° to afford pale yellow needles 9.66 g (55%) m.p. 86.5°–88°. $\nu_{max}$. ($CH_2Cl_2$) 1782, 1750, 1640, 1602, 1525, 1350 cm$^{-1}$. δ ($CDCl_3$) 1.46 (3H, s, gem dimethyl), 1.63 (3H, s, gem dimethyl), 4.45 (1H, s, C-3 proton), 5.21 (2H, s, ester $CH_2$), 5.42 (1H, dd, $J_1$=2 Hz, $J_2$=4 Hz, C-6 proton), 5.70 (1H, d, J=4 Hz, C-5 proton), 7.40 (5H, s, ester aromatics), 7.93 and 8.30 (4H, ABq, p-substituted aromatics) and 8.73 (1H, d, J=2 Hz, benzylidene proton).

(b) Benzyl N-p-nitrobenzylidene-6,α-hydroxymethyl-6,β-aminopenicillanate

N-p-nitrobenzylidene-6-aminopenicillanic acid benzyl ester (1.76 g, 0.004 mol) and anhydrous potassium carbonate (0.55 g, 0.004 mol) were dissolved in dry DMF (20 ml) and cooled in an ice-bath. Meanwhile, anhydrous paraformaldehyde (1.00 g) was heated to 150°–180° under a stream of dry nitrogen, and the resulting gaseous mixture was passed over the above stirred solution. After completion of the depolymerisation of the paraformaldehyde, the reaction solution was allowed to warm to ambient temperature and stirred for two and a half hours. It was then poured into ether (≃ 150 ml) and the resulting mixture was washed well with water (6×50 ml) and brine (3×50 ml). The yellow organic solution was dried over magnesium sulphate, filtered and evaporated to dryness to afford the title compound as a yellow foam (1.69 g, 89%). $\nu_{max}$. ($CH_2Cl_2$) 3675, 3580, 1770, 1750, 1640, 1602, 1525, 1350 cm$^{-1}$. δ ($CDCl_3$) 1.41 (3H, s, gem dimethyl), 1.53 (3H, s, gem dimethyl), 4.19 (2H, m, 6-$CH_2$), 4.41 (1H, s, C-3 proton), 4.90 (1H, br.s, —OH), 5.25 (2H, s, ester $CH_2$), 5.60 (1H, s, C-5 proton), 7.49 (5H, s, ester aromatics), 8.02 and 8.38 (4H, ABq, p-substituted aromatics) and 8.91 (1H, s, benzylidene proton).

(c) Benzyl 6,α-hydroxymethyl-6,β-aminopenicillanate

N-p-nitrobenzylidene-6,α-hydroxymethyl-6,β-amino penicillanic acid benzyl ester (1.60 g, 0.0034 mol) was dissolved in ethyl acetate (20 ml) and a solution of p-toluene sulphonic acid monohydrate (0.93 g, 0.0049 mol) in ethyl acetate (30 ml) was added dropwise with stirring at ambient temperature. Precipitation occurred almost immediately and the mixture was stirred at room temperature for three hours. The product was then filtered off and washed well with ethyl acetate. It was dried in vacuo over $P_2O_5$ to afford the tosylate salt of benzyl 6,α-hydroxymethyl-6,β-aminopenicillanate as a white solid (1.28 g, 72%). $\nu_{max}$. (KBr) 3540, 3400, 1783, 1758, 1735, 1208 cm$^{-1}$. δ [($CD_3$)$_2$SO] 1.40 (3H, s, gem dimethyl), 1.62 (3H, s, gem dimethyl), 2.31 (3H, s, p-TSA methyl), 3.95 (2H, m, 6-$CH_2$), 4.64 (1H, s, C-3 proton), 5.30 (2H, s, ester $CH_2$) 5.68 (1H, s, C-5 proton), 7.00–7.85 (9H, m, aromatics) and 7.85–9.70 (4H, v. br. s, $N^{\oplus}H_3$ and OH). The title compound was liberated from its toslylate salt by treatment with dilute sodium bicarbonate solution and extraction into ethyl acetate (3×30 ml). The combined organic extracts were washed with brine (3×30 ml) and dried over magnesium sulphate, before being filtered and evaporated to dryness to afford benzyl 6,α-hydroxymethyl-6,β-aminopenicillanate as an oil in 97% yield. $\nu_{max}$. ($CH_2Cl_2$) 3600, 3480, 1778, 1748, 1602, 1202 cm$^{-1}$. δ ($CDCl_3$) 1.40 (3H, s, gem dimethyl), 3.05 (3H, br. s, $NH_2$ and OH), 3.92 (2H, m, 6-$CH_2$), 4.50 (1H, s, C-3 proton), 5.21 (2H, s, ester $CH_2$), 5.49 (1H, s, C-5 proton) and 7.43 (5H, s, ester aromatics.

(d) Benzyl 6,α-hydroxymethyl-6,β-[D,α'-(p-nitrobenzyloxycarbonylamino-)phenylacetamido]penicillanate N-p-nitrobenzyloxycarbonyl-D-phenylglycyl chloride (0.0082 mol) in anhydrous THF (30 ml) was added dropwise, with stirring over thirty minutes to an ice-bath cooled solution of benzyl 6,α-hydroxymethyl-6,β-amino-penicillanate (2.28 g, 0.0068 mol) and pyridine (0.81 g, 0.82 ml, 0.0102 mol) in dry THF (60 ml). The solution was then allowed to warm to ambient temperature and stirred for a further two hours. The mixture was filtered, and the filtrate evaporated to dryness to leave an oil. This was dissolved in ethyl acetate and the solution washed with 0.5 N hydrochloric acid (3×30 ml), dilute sodium bicarbonate (3×30 ml) and brine (3×30 ml), before being filtered and evaporated to dryness. The product was purified by chromatography (silica) to afford the pure title compound (2.77 g, 63%). It was recrystallised from ethyl acetate/petroleum ether, m.p. 105°–119°. Found: C. 58.94; H, 5.10; N, 8.08. $C_{32}H_{32}N_4O_9S$ requires: C, 59.25; H, 4.97; N, 8.64%. $\nu_{max}$. ($CH_2Cl_2$) 3400, 3275, 1780, 1749, 1685, 1605, 1520, 1500, 1350 cm$^{-1}$. δ ($CDCl_3$) 1.02 (3H, s, gem dimethyl), 1.18 (3H, s, gem dimethyl) 4.13 (2H, ABq, 6-$CH_2$), 4.32 (1H, s, C-3 proton), 5.12 (4H, s, benzyl and p-nitrobenzyl $CH_2$'s), 5.35 (1H, d, J=7 Hz, α-proton), 5.47 (1H, s, C-5 proton), 6.38 (1H, d, J=7 Hz, exchangeable with $D_2O$, α-amido proton), 7.20–7.60 (12H, m, aromatics), 7.93 (1H, s, exchangeable with $D_2O$, 6-amido proton) and 8.12 (2H, part ABq, p-nitrobenzyl aromatics). m/e 648, 586, 381, 285, 250, 136, 114, 91.

(e) 6,α-Hydroxymethyl-6,β-(D,α'-amino-phenylacetamido)penicillanic acid

Benzyl 6,α-hydroxymethyl-6,β-[D,α'(p-nitrobenzyloxycarbonylamino-)phenylacetamido]penicillanate (1.0 g, 0.0015 mol) was dissolved in a mixture of THF (10 ml), ethanol (25 ml) and water (10 ml) and hydrogenated over 10% palladium on charcoal (1.0 g) at ambient pressure and temperature for three hours. Further catalyst (1.0 g) was then added and the hydrogenolysis continued for another two hours. The catalyst was then filtered and washed well with THF and water. The filtrate was evaporated to dryness and the residue treated with toluene and re-evaporated. It was then treated with ethanol and the product precipitated with anhydrous ether. It was filtered and washed well with ether before being dried in vacuo over phosphorous pentoxide. The product was obtained as a white solid (0.50 g, 86%). $\nu_{max}$. (KBr) 1765, 1680, 1615, 1540 cm$^{-1}$.

δ [(CD₃)₂SO] 0.94 (3H, s, gem dimethyl), 1.20 (3H, s, gem dimethyl), 3.79 (2H, m, 6-CH₂), 4.16 (1H, s, C-3 proton), 5.00 (1H, s, α-proton), 5.34 (1H, s, C-5 proton), 6.00–8.50 (9H, m, 4H, exchangeable with D₂O, aromatics, N⊕H₃ and OH) and 9.40 (1H, s, exchangeable with D₂O, amido proton).

(f) 6,α-Hydroxymethyl-6,β-[D,α'-(4-ethyl-2,3-dioxopiperazine-1-carbonylamino)-phenylacetamido]penicillanic acid 6,α-Hydroxymethyl-6,β-[D,α'-aminophenylacetamido]penicillanic acid (350 mg, 0.923 mmol) and triethylamine (0.5 ml) in methylene chloride (30 ml) and THF (5 ml) were cooled to 0° and a solution of 1-chlorocarbonyl-2,3-dioxo-4-ethylpiperazine (189 mg, 0.923 mmol) in anhydrous methylene chloride (15 ml) was added dropwise. Stirring was continued at 0° for thirty minutes followed by two and a half hours at ambient temperature. The reaction mixture was then filtered and evaporated to dryness, and the residue dissolved in ethyl acetate. The organic solution was extracted with dilute sodium bicarbonate solution (3×30 ml). The aqueous solution was then acidified to pH 1.5 and extracted with ethyl acetate (3×30 ml). After washing the organic extracts with brine (3×30 ml) and drying over magnesium sulphate, they were filtered and evaporated to dryness to afford the free acid (93 mg). This was dissolved in acetone and treated with one equivalent of 2 N sodium ethyl hexanoate in methyl isobutyl ketone followed by anhydrous ether. The precipitate was filtered off, washed with ether and dried in vacuo over phosphorous pentoxide to afford the title compound as the sodium salt, 103 mg (20%). $\nu_{max}$. (KBr) 1765, 1715, 1675, 1610, 1510, 1190 cm⁻¹. δ [(CD₃)₂SO] 0.80–1.50 (9H, m, gem dimethyls and —CH₂CH₃), 3.10–4.10 (m, —CH₂CH₃, piperazine protons, —CH₂OH, C-3 proton and H₂O), 5.34 (1H, s, C-5 proton), 5.57 (1H, d, J=7 Hz, α-proton), 7.10–7.60 (5H, m, aromatics), 9.11 (1H, s, 6-amido proton) and 9.82 (1H, d, J=7 Hz, α-amido proton).

EXAMPLE 2

6,α-Hydroxymethyl-6,β-[D,α'-(4-ethyl-2,3-dioxopiperazine-1-carbonylamino)-p-hydroxyphenylacetamido]-penicillanic acid (a) Benzyl 6,α-hydroxymethyl-6,β-[D,α'-(p-nitrobenzyloxycarbonylamino-)benzloxycarbonyl-4'-oxy phenylacetamido]penicillanate The title compound was prepared in 32% yield from N-p-nitrobenzyloxy carbonyl-D-(benzyloxycarbonyl-4'-oxy)phenylglycyl chloride and benzyl 6,α-hydroxymethyl-6,β-amino penicillanate in an analogous manner to that described in Example 1(d). Recrystallisation from ethyl acetate/petroleum ether afforded a sample, m.p. 78°–86°. Found: C, 59.28; H, 4.75; N, 6.70. C₄₀H₃₈N₄O₁₂S requires; C, 60.14; H, 4.80; N, 7.01%. $\nu_{max}$. (KBr) 1765, 1712, 1662, 1610, 1520, 1508 (sh), 1349, 1245, 1215 cm⁻¹. δ [(CD₃)SO] 1.09 (3H, s, gem dimethyl), 1.20 (3H, s, gem dimethyl), 4.02 (2H, m, 6-CH₂), 4.34 (1H, s, C-3 proton), 4.48 (1H, t, exchangeable with D₂O, —OH), 5.15 (1H, d, J=7 Hz, α-proton), 5.57 (1H, s, C-5 proton), 7.00–7.80 (12H, m, aromatic and α-amido protons), 8.16 (2H, part ABq, p-nitrobenzyl aromatics) and 8.21 (1H, s, exchangeable with D₂O, 6-amido proton).

(b) 6,α-Hydroxymethyl-6,β-(D,α'-amino-p-hydroxy phenylacetamido)penicillanic acid This compound was prepared in quantitative yield by hydrogenolysis of benzyl 6,α-hydroxymethyl-6,β-[D,α'-(p-nitrobenzyloxycarbonylamino-)benzyloxycarbonyl-4'-oxy phenylacetamido]penicillanate in an analogous manner to that described in Example 1(e). $\nu_{max}$. (KBr) 1765, 1675, 1602, 1518 cm⁻¹. δ (D₂O) 0.95 (3H, s, gem dimethyl), 4.02 (3H, m, 6-CH₂ and C-3 protons), 5.00 (1H, s, α-proton), 5.42 (1H, s, C-5 proton), 6.89 and 7.41 (4H, ABq, p-substituted aromatics).

(c) 6-α-Hydroxymethyl-6,β-[D,α'-(4-ethyl-2,3-dioxo-piperazine-1-carbonylamino)-p-hydroxyphenylacetamido]-penicillanic acid (i) Coupling under non-aqueous conditions 6,α-Hydroxymethyl-6,β-(D,α'-amino-p-hydroxyphenylacetamido)penicillanic acid (593 mg, 1.5 mmol) and triethylamine (606 mg, 6 mmol) in methylene chloride (40 ml) and dimethylformamide (20 ml) were cooled to 0° and a solution of 1-chlorocarbonyl-2,3-dioxo-4-ethylpiperazine (256 mg, 1.25 mmol) in anhydrous methylene chloride (10 ml) was then added dropwise with stirring over 10 minutes. The resulting solution was stirred at 0° for 30 minutes followed by 2.5 hours at ambient temperature. The reaction mixture was evaporated to dryness and the residue dissolved in ethyl acetate. The organic solution was extracted with dilute sodium bicarbonate solution (3×30 ml), and the aqueous extract was washed with ethyl acetate (3×30 ml). It was then acidified to pH 1.5 and extracted with a mixture of ethyl acetate and n-butanol (approx 3:1) (3×30 ml). After washing the combined organic extracts with brine (3×30 ml) and drying over magnesium sulphate, they were filtered and evaporated to dryness to afford the free acid. This was dissolved in acetone and treated with one equivalent of 2 N sodium ethyl hexanoate in methyl isobutyl ketone followed by anhydrous ether. The precipitate was filtered off, washed with ether and dried in vacuo over phosphorous pentoxide to afford the title compound as the sodium salt, 435 mg (60%). $\nu_{max}$ (KBr) 1765, 1712, 1678, 1610, 1512 cm⁻¹. δ [(CD₃)₂SO] 0.90–1.60 (9H, m, gem dimethyls and —CH₂CH₃), 3.20–4.10 (m, —CH₂CH₃, piperazine protons, —CH₂OH, C-3 proton and H₂O), 5.37 (1H, s, C-5 proton), 5.44 (1H, d, J=7 Hz, α-proton), 6.66 and 7.21 (4H, ABq, p-substituted aromatics), 8.92 (1H, s, exchangeable with D₂O, 6-amido proton) and 9.67 (1H, d, J=7 Hz, exchangeable with D₂O, α-amido proton).

(ii) Coupling under aqueous conditions

Aqueous sodium bicarbonate was added to a solution of 6,α-hydroxymethyl-6,β-(D,α'-amino-p-hydroxyphenylacetamido)penicillanic acid (494 mg, 1.25 mmol) in water (25 ml) and tetrahydrofuran (3 ml) until the pH reached 7.5. The solution was then cooled in an ice bath and a solution of 1-chlorocarbonyl-2,3-dioxo-4-ethyl piperazine (256 mg, 1.25 mmol) in tetrahydrofuran (10 ml) was added dropwise with stirring over 15 minutes. The solution was then allowed to warm to ambient temperature and stirred for a further hour whilst maintaining the pH at 7.5. It was then washed with ethyl acetate (3×30 ml) before being acidified to pH 1.5 with dilute hydrochloric acid. The product was extracted into ethyl acetate (3×30 ml) and the combined organic extracts were washed with brine (3×30 ml), dried over magnesium sulphate, filtered and evaporated to dryness to afford the free acid as a white solid 115 mg. This was dissolved in acetone and treated with the theoretical amount of sodium ethyl hexanoate in methyl isobutyl ketone followed by anhydrous ether. The resulting precipitate was filtered and washed with ether to afford the title compound as the sodium salt 10.8 mg (15%).

EXAMPLE 3

6,α-Hydroxymethyl-6,β-[DL-α'-(4-ethyl-2,3-dioxopiperazine-1-carbonylamino)2-aminothiazole-4-acetamido]penicillanic acid (a) Benzyl 6,α-hydroxymethyl-6,β-[anti-α'-methoximino-2-(4'-nitrobenzyloxycarbonylamino)thiazol-4-acetamido]-pencillanate Anti-α-methoxyimino 2-(4-nitrobenzyloxycarbonyl)aminothiazole-4-acetic acid (1.14 g, 3 mmole) was dissolved in redistilled dimethyl formamide (10 ml) together with benzyl 6,β-amino-6,α-hydroxymethyl penicillanate (1.02 g, 3 mmole). 1-Hydroxybenzotriazole monohydrate (0.46 g, 3 mmole) was added and the solution stirred at 0°. Finally a solution of N,N'-dicyclohexylcarbodi-imide (0.62 g, 3 mmole) in further dimethylformamide (2 ml) was added and stirring continued, allowing the mixture to regain ambient temperature. After 4 h the precipitated N,N'-dicyclohexylurea was filtered, washed with a little ethyl acetate, and the combined filtrate evaporated to dryness. The residue was redissolved in ethyl acetate (20 ml) and a further small quantity of the urea filtered off. The filtrate was washed sequentially with 0.5 M hydrochloric acid (2×20 ml), water (20 ml), 1.0 M sodium hydrogen carbonate (3×20 ml), water (20 ml) and brine, then dried over anhydrous sodium sulphate and evaporated to a yellow gum. Trituration with ether-petrol gave crude solid product, which was recrystallised from chloroform-ethylacetate-ether to give the protected penicillin as small colourless needles 0.91 g (44%); m.p. 113°–8°; $R_f$ 0.70 in chloroform:methanol, 9:1; δ (CDCl$_3$) 1.36 and 1.62 (6H, 2s, C-2 methyls), 4.25 (3H, s, $\underline{CH}_3O$—N), 4.43 (1H, s, C-3H), 4.1–4.5 (2H, br m, becoming ABqt [J11 Hz] on D$_2$O exchange, C—$\underline{CH}_2$—OH), 5.20 (2H, s, O$_2$NC$_6$H$_4\underline{CH}_2$O), 5.45 (1H, s, C-5H), 5.30 (2H, ABqt, [J12 Hz], C$_6$H$_5\underline{CH}_2$O), 7.36 (5H, s, C$_6$H$_5$), 7.60 and 8.20 (4H, dd, O$_2$NC$_6$H$_4\underline{CH}_2$), 9.04 (1H, s, thiazole C-5H), 11.0 (1H, br s, D$_2$O exchanged, NH). Found: C, 50.8; H, 4.4; N, 11.9. C$_{30}$H$_{30}$N$_6$O$_{10}$S$_2$.½H$_2$O requires: C, 50.9; H, 4.4; N, 11.9%.

Concentration of the recrystallisation mother liquors gave a second crop of less pure material (0.21 g), which was subjected to chromatography on silica gel, eluting with ethyl acetate:petrol, 2:1. The first-eluted species was shown (nmr) to be an N,O-diacylated product, $R_f$ 0.85 in chloroform:methanol, 9:1. Further elution gave the title compound in purity equal to that of the first crop, raising the yield to about 50%.

(b) 6,α-Hydroxymethyl-6,β-[DL-α'-amino-2-aminothiazole-4-acetamido]penicillanic acid The preceding protected derivative (0.8 g, 1.15 mmole) was dissolved in a mixture of tetrahydrofuran:ethanol:water, 2:1:1 (20 ml). 10% palladium on charcoal (0.8 g) was added and the mixture hydrogenated. After 1.25 h uptake of hydrogen had ceased; the catalyst was filtered and a fresh batch (0.8 g) added, then hydrogenation was resumed for a further 3.5 h. The catalyst was again changed after this time and hydrogenation continued for a further 16 h. After this time the catalyst was filtered off and the filtrate concentrated to dryness, then partitioned between water (10 ml) and ethyl acetate (3×10 ml). Lyophilisation of the aqueous gave the penicillin 250 mg (54%); $R_f$ 0.07 in n-butanol:acetic acid:water, 4:1:1, δ[(CD$_3$)$_2$SO] 1.1–1.6 (6H, m, C-2 methyls, diastereoisomers), 3.78 (2H, ABqt, J11 Hz, C—$\underline{CH}_2$—OH), 4.05 (1H, s, C-3H), 4.60 and 4.66 (1H, 2s, α-CH's, diastereisomers), 5.40 (1H, s, C-5H), 6.50 (1H, s, thiazole C-5H), 6.90 (2H, br s, —NH$_2$).

(c) 6,α-Hydroxymethyl-6,β-[DL-α'-(4-ethyl-2,3-dioxopiperazine-1-carbonylamino)2-aminothiazole-4-acetamido]penicillanic acid The preceding hydrogenation product (190 mg, 0.47 mmole) was dissolved in a mixture at 1.0 M sodium hydrogen carbonate (5 ml) and tetrahydrofuran (3 ml) and stirred at 0°. A solution of 4-ethyl-2,3-dioxopiperazine-1-carbonyl chloride (120 mg, 0.59 mmole) in tetrahydrofuran (3 ml) was added dropwise. The pH of the solution dropped from 8.8 to 8.0 quite sharply, then steadied. The solution was allowed to regain ambient temperature and stirring continued for 1 h. The pH of the solution was then lowered to 3.0 and evaporated to dryness, then the residue was partitioned between water (5 ml) and ethyl acetate (3×5 ml) and the aqueous phase was lyophilised. Extraction of the desired penicillin from the residue was effected most simply by stirring with ethanol (50 ml) for 1 h. The undissolved solid was filtered off, the filtrate evaporated to dryness, redissolved in water and lyophilised to give the penicillin 130 mg (49%), $R_f$ 0.20 in n-butanol:acetic acid:water, 4:1:1, δ[(CD$_3$)$_2$SO] 1.08 (3H, t, $\underline{CH}_3$CH$_2$N), 1.27, 1.33, 1.40 and 1.47 (6H, 4s, C-2 methyls, diastereoisomers), 3.2–4.0 (8H, m, 3 x $\underline{CH}_2$N and C—$\underline{CH}_2$OH), 4.24 (1H, s, C-3H), 5.43 (2H, m, 2s on D$_2$O exchange, α-CH and C-5H), 6.46 and 6.55 (1H, 2s, thiazole C-5H's, diastereoisomers), 7.0 (2H, br s, D$_2$O exchanged, thiazole C-2 NH$_2$), 8.83 (1H, brs, D$_2$O exchanged, C-6 NH), 9.60 (1H, br d, D$_2$O exchanged, α-NH).

EXAMPLE 4

(a) Benzyl 6,α-formyloxymethyl-6,β-[D,α'-(4-ethyl-2,3-dioxopiperazine-1-carbonylamino)phenylacetamido penicillanate Benzyl 6,α-hydroxymethyl-6,β-[D,α'-(4-ethyl-2,3-dioxopiperazine-1-carbonylamino)phenylacetamido]-penicillanate (0.10 g, 0.16 mmol) in pyridine (2 ml) at −40° C. was treated with acetic formic anhydride (0.08 ml, 2.1 mmol) and the reaction mixture was allowed to warm to room temperature over 1 hour. Pyridine was removed by evaporation under reduced pressure and the residue was diluted with ethyl acetate (25 ml), washed with N HCl (2×25 ml), N sodium bicarbonate solution (2×25 ml), brine (2×25 ml) dried over magnesium sulphate and evaporated, and chromatographed on silica gel (5:1 petrol:ethyl acetate) to give the title compound (101 mg, 96%) δ (CDCl$_3$) 1.22 (9H, m, 2 x CH$_3$, NCH$_2\underline{CH}_3$), 3.57 (4H, m, $\underline{NCH}_2$, piperazine CH$_2$), 3.66 (2H, m, piperazine CH$_2$) 4.35 (1H, s, C$_3$ proton), 4.69 (2H, s, CH$_2$O), 5.18 (2H, s, $\underline{PhCH}_2$), 5.53 (1H, s, C5-proton), 5.65 (1H, d, J 6.5 Hz, α-proton), 7.36 (11H, m, aromatic and NH protons), 8.03 (1H, s, CHO), 10.67 (1H, d, J 6.5 Hz, NH). $\nu_{max}$. (CH$_2$Cl$_2$) 1685, 1715, 1780, 2930, 3290 cm$^{-1}$.

(b)

6,α-Formyloxymethyl-6,β-[D,α'-(4-ethyl-2,3-dioxopiperazine-1-carbonylamino)-phenylacetamido]penicillanic acid The benzyl ester from the previous example (101 mg, 0.15 mmol) in THF (5 ml) was added to prehydrogenated 10% palladium on charcoal (100 mg) in THF (5 ml), water (1 ml). After shaking with hydrogen for 0.5 hours, the catalyst was filtered from the solution and washed well with N sodium bicarbonate solution (40 ml). The filtrate was washed with ethyl acetate (2×40 ml), acidified to pH 1.5 with 1 N-hydrochloric acid and extracted with ethyl acetate (3×40 ml). The combined extracts were washed with brine, dried and evaporated to give the title compound (46 mg, 51%), δ [(CD$_3$)$_2$CO] 1.12, 1.35 (6H, 2s, 2 x CH$_3$) 1.20 (3H, t, NCH$_2$CH$_3$), 3.3–3.8 (4H, m, NCH$_2$ and piperazine CH$_2$), 3.8–4.3 (4H, m, CH$_2$O and piperazine CH$_2$), 4.70 (1H, s, C3-proton), 5.57 (1H, s, C5-proton), 5.72 (1H, d, J 6 Hz, α-proton) 7.45 (5H, m, aromatic protons), 8.25 (1H, s, CHO), 8.48 (1H, s, NH), 10.08 (1H, d, J 6 Hz, NH). However, preparation of the sodium salt by precipitation from acetone using 2 N sodium ethyl hexanoate in methyl isobutyl ketone gave an appreciable amount of the parent 6-hydroxymethyl penicillin and in the solvents used for h.p.l.c. reconversion to the 6-hydroxymethyl compound was complete and instantaneous.

BIOLOGICAL DATA
MIC values (μg/ml) of the compounds of Examples 1 and 2 against a number of organisms important in human infections

| Organism | Compound of Example No. | | | | |
|---|---|---|---|---|---|
| | 1 | | 2 | | 3 |
| | Agar | Broth | Agar | Broth | Agar |
| E. coli JT 4 | 100 | | 100 | | >100 |
| E. coli JT 425 | 50 | | 50 | | 100 |
| E. coli NCTC 10413 | 25 | 10 | 5.0 | 5.0 | 10 |
| Ps. aeruginosa NCTC 10662 | >100 | | >100 | | >100 |
| Ps. aeruginosa NCTC 10662 10$^{-2}$ | >100 | | >100 | | >100 |
| Ps. aeruginosa | >100 | | >100 | | >Dalgleish 10$^{-2}$ |
| S. marcescens US 32 | 50 | | 5.0 | | 50 |
| K. aerogenes A | 5.0 | 100 | 2.5 | 1.0 | 1.0 |
| E. cloacae N1 | 25 | | 5.0 | | 25 |
| P. mirabilis C 977 | 10 | | 2.5 | | 10 |
| P. mirabilis 889 | 5 | | 2.5 | | 10 |
| P. morganii | 25 | | 5.0 | | 10 |
| P. rettgeri | 50 | | 5.0 | | 25 |
| B. subtilis | >100 | | >100 | | >100 |
| S. aureus Oxford | >100 | | >100 | | >100 |
| S. aureus Russell | >100 | | >100 | | >100 |
| N. catarrhalis 1502 | 1.0 | | 1.0 | | — |
| S. faecalis I | >100 | | >100 | | 100 |
| S. pyogenes ON 10 | 25 | | 2.5 | | >100 |

We claim:
1. A compound of formula (I) or a pharmaceutically acceptable salt or in-vivo hydrolysable ester thereof:

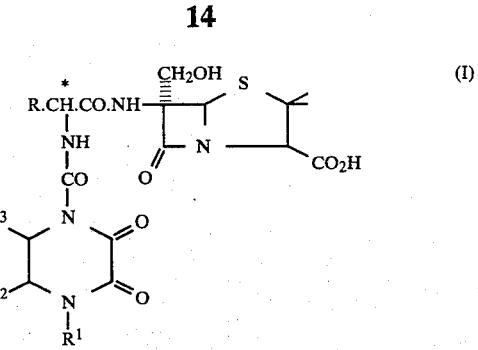

wherein
R is phenyl, 4-hydroxy phenyl, or a 5- or 6-membered heterocyclic ring containing up to three heteroatoms selected from oxygen, sulphur or nitrogen, optionally substituted with hydroxy, amino, halogen or C$_{1-6}$ alkoxy;
R$^1$ represents hydrogen or C$_{1-6}$ alkyl;
R$^2$ and R$^3$ are the same or different and represent hydrogen, C$_{1-6}$ alkyl, halogen, amino, hydroxy, or C$_{1-6}$ alkoxy.

2. A compound as claimed in claim 1 wherein the carbon atom marked * in formula (I) is in the D configuration.

3. A compound as claimed in claim 1 wherein R is phenyl or 4-hydroxyphenyl, 2-thienyl, 3-thienyl or 2-amino-4-thiazolyl.

4. A compound as claimed in claim 1 wherein R$^1$, R$^2$ and R$^3$ may be the same or different and each represents methyl, ethyl, n- and iso-propyl, n, sec-, iso- and tert-butyl.

5. A compound as claimed in claim 1 wherein R$^1$ is ethyl.

6. A compound as claimed in claim 1 wherein R$^2$ and R$^3$ are hydrogen.

7. A compound as claimed in claim 1 or a pharmaceutically acceptable salt or in vivo hydrolysable ester thereof which is:
6,α-hydroxymethyl-6,β-[D,α'-(4-ethyl-2,3-dioxopiperazine-1-carbonylamino)-phenylacetamido]-penicillanic acid;
6,α-hydroxymethyl-6,β-[D,α'-(4-ethyl-2,3-dioxopiperazine-1-carbonylamino)-p-hydroxy-phenylacetamido]penicillanic acid; or
6,α-hydroxymethyl-6,β-[DL-α'-(4-ethyl-2,3-dioxopiperazine-1-carbonylamino)-2-aminothiazole-4-acetamido]penicillanic acid.

8. A pharmaceutical composition having antibacterial activity comprising an antibacterially effective amount of a compound as claimed in claim 1 together with a pharmaceutical carrier or excipient.

9. A pharmaceutical composition according to claim 8 which also comprises a compound of formula (VIII) or a pharmaceutically acceptable salt or ester thereof:

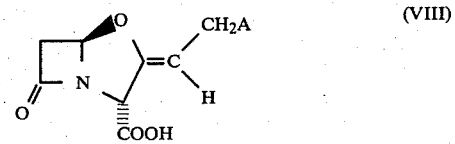

wherein A is hydroxyl, substituted hydroxyl, thiol, substituted thiol, amino, mono- or di-hydrocarbyl-substituted amino, or mono- or di-acylamino.

10. A method of treating bacterial infections which comprises the administration to a host in need thereof of an effective amount of a composition of claim 8.

11. A method of treating bacterial infections which comprises the administration to a host in need thereof of an effective amount of a composition of claim 9.

* * * * *